(12) United States Patent
Smith et al.

(10) Patent No.: US 9,948,091 B1
(45) Date of Patent: Apr. 17, 2018

(54) INTEGRATED DEFIBRILLATION PULSE PROTECTOR

(71) Applicant: Maxim Integrated Products, Inc., San Jose, CA (US)

(72) Inventors: Douglas Stuart Smith, Milpitas, CA (US); Vladislav Vashchenko, Palo Alto, CA (US); Augusto Tazzoli, San Jose, CA (US); Sudhir Mulpuru, Milpitas, CA (US); Lawrence Richard Skrenes, Hartland, WI (US)

(73) Assignee: Maxim Integrated Products, Inc., San Jose, CA (US)

( * ) Notice: Subject to any disclaimer, the term of this patent is extended or adjusted under 35 U.S.C. 154(b) by 0 days.

(21) Appl. No.: 15/169,438

(22) Filed: May 31, 2016

Related U.S. Application Data

(60) Provisional application No. 62/170,829, filed on Jun. 4, 2015.

(51) Int. Cl.
*A61B 5/00* (2006.01)
*H02H 9/04* (2006.01)
*A61B 5/0408* (2006.01)
*A61B 5/0428* (2006.01)
*A61N 1/39* (2006.01)

(52) U.S. Cl.
CPC ........... *H02H 9/045* (2013.01); *A61B 5/0408* (2013.01); *A61B 5/0428* (2013.01); *A61N 1/3931* (2013.01)

(58) Field of Classification Search
CPC .......... H02H 9/00; H02H 9/005; H02H 9/045; H02H 9/02; A61B 5/0428; A61B 5/0424; A61N 1/3925–1/3943
See application file for complete search history.

(56) References Cited

U.S. PATENT DOCUMENTS

| | | | |
|---|---|---|---|
| 2002/0053704 A1* | 5/2002 | Avery | H01L 27/0255 257/361 |
| 2004/0201033 A1* | 10/2004 | Russ | H01L 29/87 257/107 |
| 2008/0218922 A1* | 9/2008 | Mallikararjunaswamy | H01L 27/0262 361/91.6 |

* cited by examiner

*Primary Examiner* — Scott Getzow
(74) *Attorney, Agent, or Firm* — North Weber & Baugh LLP

(57) ABSTRACT

Silicon-controlled rectifier (SCR) based circuit for ECG protection under defibrillator pulse is disclosed. The SCR-based clamp is a symmetric structure for dual-direction voltage tolerance protection based on two anti-series P-well/N-well lateral blocking junctions isolated from P-substrate by the N-buried layer. The injector regions (n+/p+) are substantially lengthened in order to accommodate a larger number of contact rows than typically used for ESD pulses specification. A stack of metal layers may also be used to provide high current and heat-sink capability with each electrode metal layer fully filled with VIAs.

20 Claims, 2 Drawing Sheets

US 9,948,091 B1

INTEGRATED DEFIBRILLATION PULSE PROTECTOR

CROSS REFERENCE TO RELATED APPLICATION

The application claims priority to U.S. Provisional Patent Application No. 62/170,829, entitled "Integrated Defibrillation Pulse Protector," listing as inventors, Douglas Stuart Smith, Vladislav Vashchenko, Augusto Tazzoli, Sudhir Mulpuru, and Lawrence Richard Skrenes, and filed Jun. 4, 2015, the subject matter of which is hereby incorporated herein by reference in its entirety.

BACKGROUND

A. Technical Field

The present invention relates generally to the field of defibrillator pulse protector and more particularly to SCR-based defibrillator pulse protector.

B. Background of the Invention

Defibrillation is a common treatment for life-threatening cardiac dysrhythmias, ventricular fibrillation and pulseless ventricular tachycardia. Defibrillation consists of delivering desired electrical energy to the heart of a patient with a device called a defibrillator. The connection between the defibrillator and the patient consists of a pair of electrodes, each provided with electrically conductive gel in order to ensure a good connection and to minimize electrical resistance. Typically, up to 5 kV voltage and energy up to 360 J are necessary to penetrate the chest and shock the heart.

It is not uncommon that several pieces of equipment, such as Electrocardiography (ECG) electrode for monitoring, are also attached to the patient at the same time of defibrillation treatment. The voltage delivered to the patient during defibrillation treatment is generally above the limit of low voltage electrical circuits of the ECG monitoring equipment. Therefore, a protection circuit is required to limit the voltage across sensors electrodes during a highly energetic defibrillator pulse to a desired level for the ECG equipment.

Argon or Neon bulbs haven been used for defibrillator pulse protection to limit the voltage during defibrillation pulse. Due to the gas discharge tube's rather high ON voltage, a second protective network is needed to further lower the input voltage fed into the ECG equipment. Furthermore, the bulky and thickness of the gas discharge tube makes it difficult to be packaged within thin, flexible unobtrusive form factors for modern wearable medical devices.

Therefore, it would be desirable to have a system, device, and method to have an ECG protection circuit with compact size, low ON voltage, and high current shunting capability.

SUMMARY OF THE INVENTION

Certain embodiments of the invention provide for systems, devices, and methods for ECG protection under defibrillator pulses.

According to various embodiments of the invention, various means for defibrillator pulses protection are disclosed. The protection may be implemented by adoption of a low resistance and high current-capability silicon-controlled rectifier (SCR) based clamp to shunt away excessive defibrillation pulse energy and limit the voltage for ECG monitor equipment.

In certain embodiments, the SCR-based clamp is a symmetric structure for dual-direction voltage tolerance protection based on two anti-series P-well/N-well lateral blocking junctions isolated from P-substrate by the N-buried layer. Each P-well region encloses n+ and p+ contact pairs playing an interchangeable role of corresponding emitters and bases depending on the current direction. The basic SCR intrinsically triggers when a voltage of about 10.5 V is applied across its terminals (or electrodes), and then goes into a low voltage state (around 2 V at 100 mA) with an on-state resistance of around 1Ω. This low voltage state guaranties a good voltage protection for low voltage electronic devices connected to its terminals even under high defibrillation pulse.

In certain embodiments, the injector regions (n+/p+) are substantially lengthened in order to accommodate a larger number of contact rows than typically used for ESD pulses specification. This simultaneously accommodates a larger number of contacts, which is beneficial to push forward electromigration limits, and to increase the silicon volume involved in heat dissipation. Furthermore, stack of metal layers may be used to provide high current and heat-sink capability with each electrode metal layer fully filled with VIAs.

Although the device is designed as a defibrillator pulse protector, other applications can be envisioned in many other areas of the microelectronic industry. Examples can be seen in automotive or portable applications as a low parasitic, very robust, general purpose transient voltage suppressor (TVS).

BRIEF DESCRIPTION OF THE DRAWINGS

Reference will be made to exemplary embodiments of the present invention that are illustrated in the accompanying figures. Those figures are intended to be illustrative, rather than limiting. Although the present invention is generally described in the context of those embodiments, it is not intended by so doing to limit the scope of the present invention to the particular features of the embodiments depicted and described.

One skilled in the art will recognize that various implementations and embodiments of the invention may be practiced in accordance with the specification. All of these implementations and embodiments are intended to be included within the scope of the invention.

DETAILED DESCRIPTION OF THE PREFERRED EMBODIMENTS

In the following description, for the purpose of explanation, specific details are set forth in order to provide an understanding of the present invention. The present invention may, however, be practiced without some or all of these details. The embodiments of the present invention described below may be incorporated into a number of different electrical components, circuits, devices, and systems. Structures and devices shown in block diagram are illustrative of exemplary embodiments of the present invention and are not to be used as a pretext by which to obscure broad teachings of the present invention. Connections between components within the figures are not intended to be limited to direct connections. Rather, connections between components may be modified, re-formatted, or otherwise changed by intermediary components.

When the specification makes reference to "one embodiment" or to "an embodiment", it is intended to mean that a particular feature, structure, characteristic, or function described in connection with the embodiment being discussed is included in at least one contemplated embodiment of the present invention. Thus, the appearance of the phrase, "in one embodiment," in different places in the specification does not constitute a plurality of references to a single embodiment of the present invention.

Various embodiments of the invention are used for systems, devices and methods for SCR-based defibrillator pulse protection. The protection may be implemented by adoption of a low ON resistance and high current-capability silicon-controlled rectifier (SCR) based structure to shunt away excessive defibrillation pulse energy for ECG monitor equipment. Furthermore, embodiments of the invention are applicable to a diverse set of techniques and methods.

Figure 1:
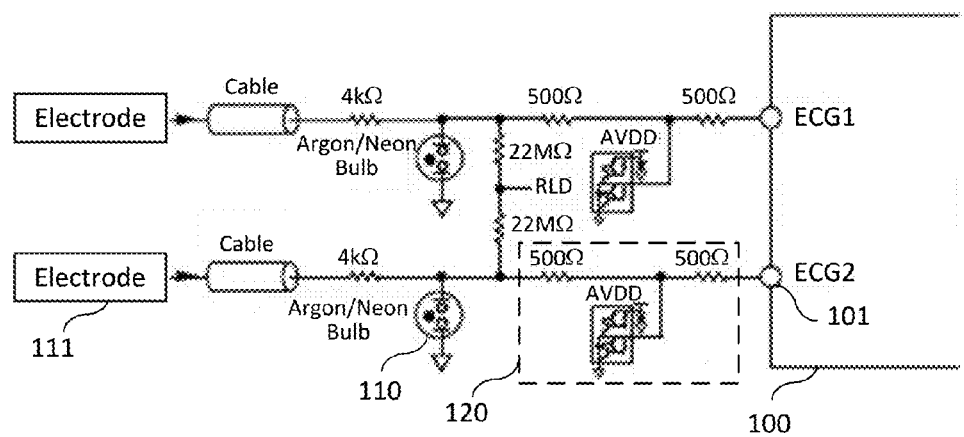
FIG. 1 is a prior art defibrillator pulse protection circuit.

FIG. 1 is a prior art defibrillator pulse protection circuit using Argon or Neon bulbs. A gas discharge tube 110 is coupled between an ECG terminal or electrode 111 and an input port 101 of the ECG monitoring equipment 100. The gas discharge tube 110 switches on when the ECG electrode 111 has a high voltage input and thus limits the voltage across the ECG monitoring equipment 100. However, due to the high ON voltage of the gas discharge tube 110, the defibrillator pulse protection circuit requires a secondary clamp circuit 120 to further lower the voltage input to the ECG monitoring equipment 100. Furthermore, the bulky and thickness of the gas discharge tube makes it difficult to be packaged within thin, flexible unobtrusive form factors for modern wearable medical devices.

Figure 2:
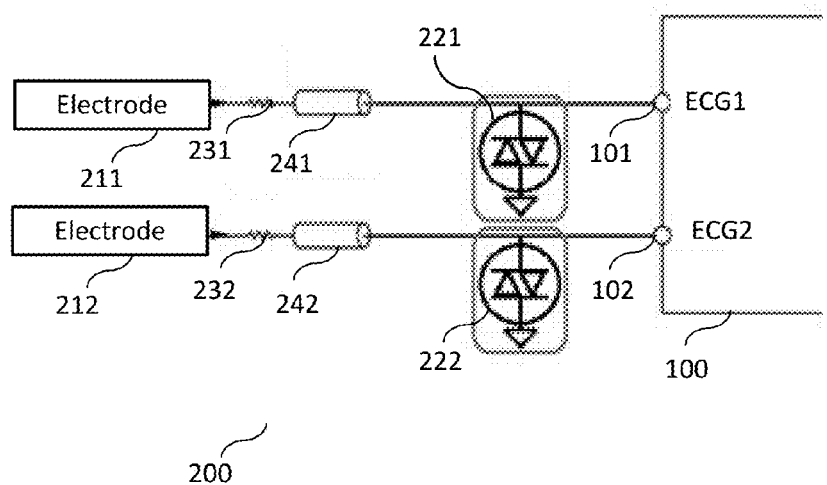
FIG. 2 is an exemplary structure overview of a SCR based defibrillator pulse protection circuit according to various embodiments of the invention.

FIG. 2 is an exemplary structure overview of a SCR based defibrillator pulse protection circuit according to various embodiments of the invention. The protection circuit 200 couples between ECG electrodes (211 and 212) and ECG input ports (101 and 102) of the ECG monitoring equipment 100. The ECG electrodes may be placed near or away from electrodes for defibrillation pluses. Each ECG electrode (211 or 212) is connected to an ECG input port (101 or 102) through a high voltage resistor (231 or 232) and a connection cable (241 or 242). A SCR-based clamp (221 or 222) couples to the ECG input port (101 or 102) in parallel and functions to shunt excessive electrical energy from the ECG electrode (211 or 212).

The SCR-based clamp (221 or 222) does not require external triggering circuit or signal. Instead, the SCR-based clamp (221 or 222) intrinsically triggers when a voltage applied across its terminals (or electrodes) reaches a triggering threshold, and then goes into a low voltage state (or ON state) with a low ON-state resistance. The triggering threshold is low compared to spark-gap based solutions and this makes superfluous the use of a secondary stage protection circuitry as shown in FIG. 1. In one embodiment, the triggering threshold is around 10V. Furthermore, the intrinsic triggering mechanism does not require external triggering circuit or signal, and thus makes the protection circuit more compact.

In one embodiment, at ON-state, the SCR-based clamp (221 or 222) has resistance around 1Ω and around 2 V across its terminals under 100 mA current, which guaranties a good voltage protection for the ECG monitoring equipment 100 (and any device coupled to the clamp). The high voltage resistor (231 or 232) limits the current through the SCR-based clamp (221 or 222) when the clamp is at ON-state. In one embodiment, the high voltage resistor (231 or 232) has a resistance of 4Ω and has a power ratio high enough to handle excessive electrical energy input from the ECG electrodes (211 and 212).

Although only two sets of electrodes and input ports shown in FIG. 2, it is understood that the ECG monitoring equipment 100 may comprise more than two electrodes and the high voltage resistor coupling to each electrode may or may not be the same, depending on the location of the electrode.

Figure 3:
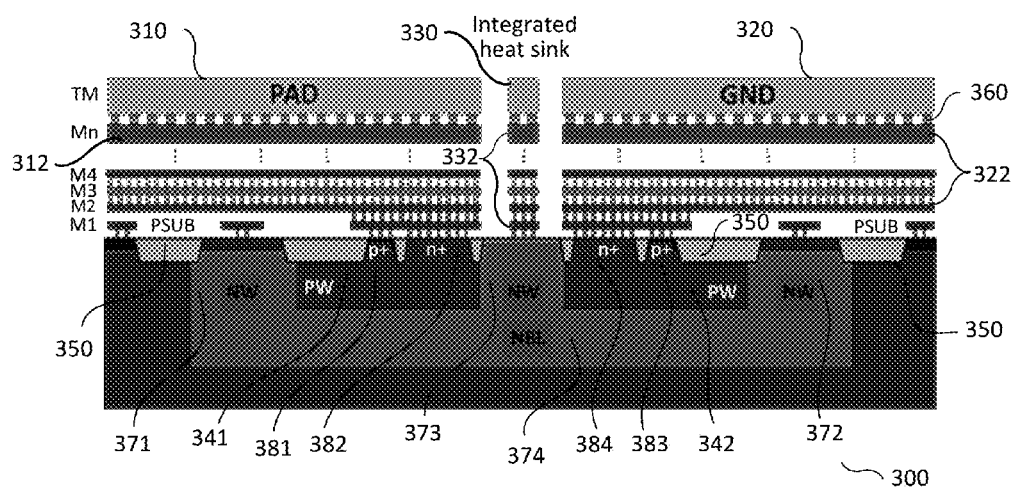
FIG. 3 is an exemplary cross-section structure overview of a SCR-based clamp for according to various embodiments of the invention.

FIG. 3 is an exemplary cross-section structure overview of a SCR-based clamp according to various embodiments of the invention. The cross-section structure 300 of the SCR-based clamp comprises a PAD electrode 310, a ground electrode 320 and an optional integrated heat sink 330 electrically isolated from both the PAD electrode 310 and the ground electrode 320. It can be seen from FIG. 3 that the SCR-based clamp is symmetric with the PAD electrode 310 and the ground electrode 320 symmetrically placed on both sides of the integrated heat sink 330.

The cross-section structure 300 further comprises a first plurality stacks metal layers 312, a second plurality stacks metal layers 322 and a third plurality stacks metal layers 332. Each metal layer is fully filled with VIAs 360 for electrical coupling to other metal layers. The first plurality stacks metal layers 312, the second plurality stacks metal layers 322 and the third plurality stacks metal layers 332 are electrically coupled to the PAD electrode 310, the ground electrode 320 and the heat sink 330 respectively. The centered heat sink 330 improves the heat dissipation from the center area of the clamp, which has the highest peak temperature within the clamp.

The cross-section structure 300 further comprises a first n-well (NW) region 371, a second NW region 372 and a third NW region 373. The first NW region 371 and the second NW region 372 are also symmetrically placed on both sides of the third NW region 373. All the NW regions are joined by an N+ buried layer (NBL) 374 placed beneath the NW regions. A first p-well (PW) region 341 is disposed between the first NW region 371 and the third NW region 373. A second p-well (PW) region 342 is disposed between the second NW region 372 and the third NW region 373.

P+ and n+ regions are created, forming a first p+ contact 381 and a first n+ contact 382 in the first PW region 341 and a second p+ contact 383 and a second n+ contact 384 in the second PW region 342. The first p+ contact 381 and the first n+ contact 382 are symmetrically disposed against the second p+ contact 383 and the second n+ contact 384. Furthermore, the first p+ contact 381 and the first n+ contact 382 are electrically coupled to the PAD electrode 310 via the first plurality stacks metal layers 312. Similarly, the second p+ contact 383 and the second n+ contact 384 are electrically coupled to the ground electrode 320 via the second plurality stacks metal layers 322. The p+ and n+ regions may be made via diffusion or dopant implantation process.

The p+ contact and n+ contact in each PW region play an interchangeable role of corresponding emitters and bases depending on the current direction. The symmetrical SCR based structure provides a dual-direction voltage tolerance protection based on two anti-series PW/NW lateral blocking junctions isolated from P-substrate (PSUB) by the N-buried layer 350. The SCR-based clamp (221 or 222) intrinsically triggers when a voltage across (either positively or negatively) the PAD electrode and the ground electrode reaches a triggering threshold, and then goes into a low voltage state (or ON state) with a low ON-state resistance. In one embodiment, the triggering threshold is around 10 V. Furthermore, the intrinsic triggering mechanism does not require external triggering circuit or signal, and thus makes the protection circuit more compact. In another embodiment, at ON-state, the SCR-based clamp has resistance around 1Ω and around 2 V across its terminals under 100 mA current, which guaranties a good voltage protection for the ECG monitoring equipment 100 (and any device coupled to the clamp). One skilled in the art will recognize that various implementations may be realized other than the exemplary cross-section structure shown in FIG. 3. In one embodiment, the isolation of the NBL or the deep NW region may be applied to the left (PAD) side of the structure only. In another embodiment, the NBL-NEPI layer (used for Bipolar-CMOS-DMOS (BCD) process) may be replaced by deep n-well (NW) with no side NW isolation scheme for CMOS process.

Figure 4:
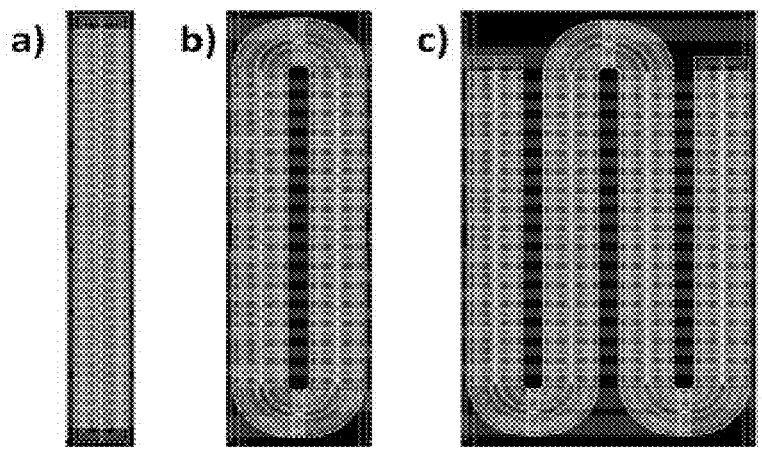
FIG. 4 shows exemplary layouts of the SCR-based clamp according to various embodiments of the invention.

FIG. 4 shows three exemplary layouts of the SCR-based clamp according to various embodiments of the invention. FIG. 4 (a) shows a rectilinear layout, FIG. 4 (b) shows race-track loop layout and FIG. 4 (c) shows a winding layout. All of layouts may be seen as a single device, with a total device active area spanning from 190 to 2,500 μm². The size (length) of injector regions (n+/p+) was substantially increased in order to accommodate larger area of contact to handle excessive electrical current during defibrillation pulses. Furthermore, the injector regions (n+/p+) are wider compared to injector regions within regular ESD (electrostatic discharge) clamp devices. This allows the integration of multiple numbers of electrical contacts (like 3 on top of p+ and 7 on top of n+ in FIG. 3). This simultaneously pushes forward electromigration limits, and also increases the silicon volume involved in heat dissipation.

The curvature regions of racetrack and winding layouts are effective to avoid possible weak points caused by high-electric field concentration, current crowding, or heat localization typical of 90 degree (or in general small-radius) corner regions. Moreover, the bended layout as shown in FIGS. 4 b) and c) allows an overall more compact solution without suffering from non-uniform triggering problems traditionally limiting multi-finger devices. Although only three layouts are shown in FIG. 4, it is understood that various other layouts, such a circular or oval shaped layout, may be realized within the described architecture. Furthermore, a plurality of electrically isolated segments may be integrated on a clamp device capable of coupling to multiple input ports of ECG monitoring equipment, thus providing an additional integration convenience.

One skilled in the art will recognize that various implementations may be realized within the described architecture, all of which fall within the scope of the invention. Despite this SCR-based clamp shown in FIGS. 2-4 are designed as a defibrillator pulse protector, other applications can be envisioned in many other areas of the microelectronic industry. Examples can be seen in automotive or portable applications as a low parasitic, very robust, general purpose transient voltage suppressor (TVS).

The foregoing description of the invention has been described for purposes of clarity and understanding. It is not intended to limit the invention to the precise form disclosed. Various modifications may be possible within the scope and equivalence of the application.

The invention claimed is:

1. An electrocardiography (ECG) protection circuit comprising:
    a silicon-controlled rectifier (SCR) having an ON-state resistance, the SCR comprising:
    first and second electrodes configured to couple to a device that operates below a threshold voltage;
    first and second ECG electrodes coupled to the first and second electrodes, the first and second ECG electrodes configured to generate a first voltage that causes the threshold voltage being applied between the first and second electrodes, wherein the SCR, in response to thereto, is configured to change from the threshold voltage to an ON-state voltage that is relatively lower than the threshold voltage; and
    a monitoring device coupled to the SCR to monitor an input voltage to the monitoring device.

2. The ECG protection circuit of claim 1 further comprising resistors coupled to respective first and second ECG electrodes.

3. The ECG protection circuit of claim 1 wherein the SCR comprises a first P-well region, a second P-well region and an N-well region, the P-well regions and the N-well region, the first and second P-well regions and the N-well region forming a symmetric structure with anti-series blocking junctions for dual-direction voltage tolerance protection.

4. The ECG protection circuit of claim 3 wherein the first P-well region comprises a first n+ and p+ contact pair that electrically couples to the PAD electrode, the second P-well region comprises a second n+ and p+ contact pair electrically couples to the ground electrode, the n+ and p+ contact of both contact pairs playing an interchangeable role of corresponding emitters and bases.

5. The ECG protection circuit of claim 4 wherein the first n+ and p+ contact pair couples to the PAD electrode via a first plurality stacks of metal layers with each metal layer filled with VIAs for electrical coupling to other metal layers, wherein the second n+ and p+ contact pair couples to the ground electrode via a second plurality stacks of metal layers with each metal layer filled with VIAs for electrical coupling to other metal layers.

6. The ECG protection circuit of claim 5 wherein the SCR further comprises a third plurality stacks of metal layers coupled between a heat sink and the N-well region, each metal layer filled with VIAs for electrical coupling, the heat sink being electrically insulated from the first and second electrodes.

7. The ECG protection circuit of claim 1 wherein the SCR has one of a rectilinear layout, a race-track loop layout, and a winding layout.

8. The ECG protection circuit of claim 1 wherein each resistor has a resistance that is higher than the ON-state resistance.

9. A method for protecting an Electrocardiography (ECG) circuit, the method comprising:
    applying a first voltage between first and second ECG electrodes that are coupled to a silicon-controlled rectifier (SCR), the first voltage causes a threshold voltage across the SCR to change to an ON-state voltage that is relatively lower than the threshold voltage;
    operating the SCR at the ON-state voltage to generate a second voltage compatible with an input voltage of a monitoring device; and
    using the input voltage to operate the monitoring device.

10. The method of claim 9 wherein the threshold voltage is 10 V and the ON-state voltage is 2V.

11. The method of claim 9 wherein the SCR is configured to reduce an energy flow between the any of first and second ECG electrodes and the monitoring device.

12. The method of claim 11 wherein the SCR comprises two P-well regions and an N-well region isolated from a P-substrate by an N-buried layer, the two P-well regions and the N-well region forming a symmetric structure with anti-series blocking junctions for dual-direction voltage tolerance protection.

13. The method of claim 12 wherein each P-well region comprises a n+ and p+ contact pair, the n+ and p+ contact playing an interchangeable role of corresponding emitters and bases.

14. The method of claim 12 wherein the SCR further comprises an integrated heat-sink placed between and isolated from the electrodes coupled to both P-wells.

15. A transient voltage suppressor (TVR) comprising:
first and second electrodes configured to couple to a device that operates below a threshold voltage, the TVR configured to change, in response to the threshold voltage being applied between the first and second electrodes, from the threshold voltage to a ON-state voltage that is relatively lower than the threshold voltage.

16. The transient voltage suppressor of claim 15 further comprising a heat sink electrically isolated from both the first and second electrodes, first and second electrodes symmetrically placed on both sides of the heat sink.

17. The transient voltage suppressor of claim 15 further comprising a first contact pair that comprises a first p+ contact and a first n+ contact formed within a first P-well (PW) region.

18. The transient voltage suppressor of claim 17 further comprising a second contact pair that comprises a second p+ contact and a second n+ contact formed within a second P-well (PW) region, the first p+ contact and the first n+ contact being symmetrically disposed against the second p+ contact and the second n+ contact.

19. The transient voltage suppressor of claim 15 wherein transient voltage suppressor has one of a rectilinear layout, a race-track loop layout, and a winding layout.

20. The transient voltage suppressor of claim 15 further comprising resistors coupled to respective first and second ECG electrodes.

* * * * *